United States Patent
Habeck et al.

[11] Patent Number: 6,069,258
[45] Date of Patent: May 30, 2000

[54] COSMETIC PREPARATIONS COMPRISING PHOTOSTABLE UV-A FILTERS

[75] Inventors: Thorsten Habeck, Meckenheim; Alexander Aumüller, Neustadt; Volker Schehlmann, Römerberg; Horst Westenfelder, Neustadt; Thomas Wünsch, Speyer, all of Germany

[73] Assignee: BASF Aktiengesellschaft, Ludwigshafen, Germany

[21] Appl. No.: 09/296,240

[22] Filed: Apr. 22, 1999

Related U.S. Application Data

[62] Division of application No. 08/916,361, Aug. 22, 1997.

[30] Foreign Application Priority Data

Aug. 23, 1996 [DE] Germany ............... 196 34 229

[51] Int. Cl.⁷ ............ C07D 333/22; C07D 255/00; A61K 31/38; A61K 31/275
[52] U.S. Cl. ............ 549/76; 558/405; 514/438; 514/520
[58] Field of Search ............... 549/76; 558/405; 514/438, 520

[56] References Cited

U.S. PATENT DOCUMENTS

| | | | |
|---|---|---|---|
| 3,280,069 | 10/1966 | Knapp et al. | |
| 3,694,211 | 9/1972 | Sato et al. | |
| 4,005,095 | 1/1977 | Robba et al. | 549/76 |
| 4,382,929 | 5/1983 | Bradshaw et al. | 549/76 |
| 4,387,089 | 6/1983 | De Polo | |
| 5,756,535 | 5/1998 | Schwark et al. | 549/76 |
| 5,830,441 | 11/1998 | Wang et al. | 558/401 |

FOREIGN PATENT DOCUMENTS

| | | |
|---|---|---|
| 1 251 590 | 12/1960 | France . |
| 2 118 798 | 11/1971 | Germany . |
| 948627 | 2/1964 | United Kingdom . |
| 1 309 349 | 3/1973 | United Kingdom . |

OTHER PUBLICATIONS

Popandova–Yambolieva et al, "Reaction of pivaloylacetonitrile with aromatic aldehydes", CA 119:180490, 1993.

*Primary Examiner*—Deborah C. Lambkin
*Attorney, Agent, or Firm*—Oblon, Spivak, McClelland, Maier & Neustadt, P.C.

[57] ABSTRACT

A cosmetic preparation which comprises a sunscreen agent for protecting the human epidermis against UV light in the range from 280 to 400 nm, which comprises, in a cosmetically suitable carrier, alone or together with compounds which absorb in the UV region and are known for cosmetic preparations, as photostable UV-A filters, effective amounts of compounds of the formula I

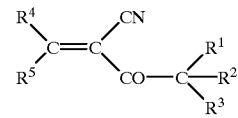

where $R^1$, $R^2$ and $R^3$ are hydrogen or aliphatic or cycloaliphatic radicals each having up to 18 carbon atoms, it being possible for any two of the radicals $R^1$, $R^2$ and $R^3$ together to form a 5- or 6-membered ring, and $R^4$ and $R^5$ are an unsubstituted or substituted aromatic or heteroaromatic radical having 5 to 12 ring atoms, and $R^5$ can additionally be hydrogen.

15 Claims, No Drawings

COSMETIC PREPARATIONS COMPRISING PHOTOSTABLE UV-A FILTERS

This application is a division of 08/916,361, filed Aug. 22, 1997, allowed.

The invention relates to the use of α-acyl-⊕-arylacrylonitriles as photostable UV-A filters in cosmetic preparations for protecting the human epidermis from UV radiation, specifically in the range from 320 to 400 nm.

The sunscreen agents employed in cosmetic preparations have the task of preventing harmful effects of sunlight on the human skin, or at least diminishing the results thereof. In addition, however, these sunscreen agents also serve to protect other ingredients from damage or breakdown by UV radiation.

The sunlight reaching the surface of the earth contains UV-B (280 to 320 nm) and UV-A (>320 nm) radiation directly adjacent to the visible light region. In the case of UV-B radiation, the effect on human skin is made particularly evident by sunburn. Accordingly, the industry supplies a large number of substances which absorb UV-B radiation and thus prevent sunburn.

Dermatological investigations have shown that UV-A radiation is also perfectly capable of inducing skin damage by, for example, damaging keratin or elastin. This reduces the elasticity and water-storage capacity of the skin, ie. the skin becomes less supple and tends to form wrinkles. The noticeably high incidence of skin cancer in areas exposed to strong sunlight shows that damage to the genetic information in the cells can evidently also be caused by sunlight, specifically by UV-A radiation. All these findings therefore make it appear necessary to develop efficient filter substances for the UV-A region.

There is a growing demand for sunscreen agents for cosmetic preparations which can be used in particular as UV-A filters and whose absorption maxima ought therefore to be in the range of about 320–380 nm. In order to achieve the required effect employing the smallest possible amount, sunscreen agents of this type should additionally have a high specific extinction. In addition, sunscreen agents for cosmetic products must also meet a large number of other requirements, for example good solubility in cosmetic oils, high stability of the emulsions produced with them, toxicological acceptability and low intrinsic odor and slight intrinsic color.

Another requirement which sunscreen agents must meet is adequate photostability. However, with the UV-A-absorbing sunscreen agents available to date, this is ensured only inadequately, if at all.

French Patent No. 2 440 933 describes 4-(1,1-dimethylethyl)-4'-methoxydibenzoylmethane as UV-A filter. It is proposed to combine this specific UV-A filter, which is sold by GIVAUDAN under the name "PARASOL 1789", with various UV-B filters in order to absorb all UV rays with a wavelength of from 280 to 380 nm.

However, this UV-A filter has, if used alone or in combination with UV-B filters, inadequate photochemical stability to ensure maintained protection of the skin during a lengthy sunbathe, which means that repeated applications at regular and short intervals are necessary if effective protection of the skin against all UV rays is desired.

This is why, as disclosed in EP 0514491, the insufficiently photostable UV-A filters should be stabilized by adding 2-cyano-3,3-diphenylacrylic esters which themselves act as filters in the UV-B region.

In addition, it has been proposed in EP 251 398 to combine chromophores which absorb UV-A and UV-B radiation in one molecule by a linker. This has the disadvantages that free combination of UV-A and UV-B filters in the cosmetic preparation is no longer possible, and that only certain combinations are possible due to difficulties in the chemical linkage of the chromophores.

It is an object of the present invention to propose sunscreen agents for cosmetic purposes which absorb in the UV-A region and which are photostable.

We have found that this object is achieved by using compounds of the formula I

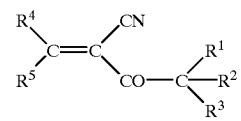

where $R^1$, $R^2$ and $R^3$ are hydrogen or aliphatic or cycloaliphatic radicals, in particular alkyl, alkenyl, cycloalkyl or cycloalkenyl radicals, each having up to 18 carbon atoms, it being possible for any two of the radicals $R^1$, $R^2$ and $R^3$ together to form a 5- or 6-membered ring, $R^4$ and $R^5$ are an unsubstituted or substituted aromatic or heteroaromatic radical having 5 to 12 ring atoms, and $R^5$ can additionally be hydrogen, as UV-A filters in cosmetic preparations for protecting the human skin from the sun's rays, alone or together with compounds which absorb in the UV region, in particular in the UV-B region, and are known for cosmetic preparations.

Preferred compounds of the formula I in this connection are those where $R^5$ is hydrogen and $R^1$, $R^2$ and $R^3$ are low molecular weight alkyl radicals.

It is particularly preferred to use compounds of the formula I where $R^5$ is hydrogen, $R^1$, $R^2$ and $R^3$ are low molecular weight alkyl radicals, eg. having 1 to 4 carbon atoms, and $R^4$ is unsubstituted or substituted thienyl or an unsubstituted or substituted 4-hydroxy- or 4-alkoxyphenyl radical.

Suitable alkoxy radicals are those having 1 to 12 carbon atoms, preferably having 1 to 8 carbon atoms.

Examples which may be mentioned are:

| | |
|---|---|
| methoxy | isopropoxy- |
| n-propoxy- | 1-methylpropoxy- |
| n-butoxy- | n-pentoxy- |
| 2-methylpropoxy- | 3-methylbutoxy- |
| 1,1-dimethylpropoxy- | 2,2-dimethylpropoxy- |
| hexoxy- | 1-methyl-1-ethylpropoxy- |
| heptoxy- | octoxy- |
| 2-ethylhexoxy- | |

The compounds to be used according to the invention are in some cases known from the chemical literature.

Novel compounds are those of the formula II

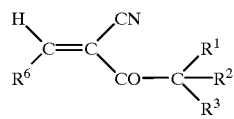

where $R^1$, $R^2$ and $R^3$ are low molecular weight alkyl radicals, eg. having 1 to 4 carbon atoms, and $R^6$ is a 2-thienyl radical which is unsubstituted or substituted by low molecular weight alkyl radicals, or is a 3,5-di-t-butyl-4-hydroxy- or alkoxyphenyl radical.

The compounds of the formula I or II to be used according to the invention can be prepared by condensation according to the equation

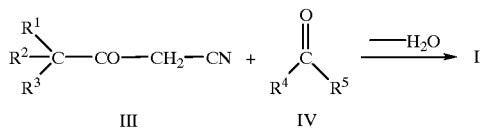

where $R^1$ to $R^5$ have the abovementioned meanings.

The cosmetic preparations comprising sunscreen agents are, as a rule, based on a carrier which comprises at least an oil phase. However, possible preparations also have only an aqueous (gel) base. Accordingly, oils, oil-in-water and water-in-oil emulsions, creams and pastes, protective lipstick compositions or gels are suitable.

Sunscreen products of these types can accordingly be in the form of a liquid, paste or solid, for example as water-in-oil creams, oil-in-water creams and lotions, aerosol foam creams, gels, oils, grease sticks, dusting powders, sprays or hydroalcoholic lotions.

Examples of conventional oil components in cosmetics are liquid paraffin, glyceryl stearate, isopropyl myristate, diisopropyl adipate, cetylstearyl 2-ethylhexanoate, hydrogenated polyisobutene, petrolatum, caprylic acid/capric acid triglycerides, microcrystalline wax, lanolin and stearic acid.

Examples of conventional cosmetic ancillary substances which may be suitable as additives are emulsifiers such as fatty alcohol ethoxylates, sorbitan fatty acid esters or lanolin derivatives, thickeners such as carboxymethylcellulose or crosslinked polyacrylic acid, preservatives and perfumes. Finally, other conventional substances absorbing in the UV-A region may also be present as long as they are stable in the overall system comprising the combination of UV-B and UV-A filters to be used according to the invention.

The present invention furthermore relates to cosmetic preparations which comprise 0.1–10% by weight, preferably 1–7% by weight, based on the total amount of the cosmetic preparation, of one or more compounds of the formula I together with compounds which absorb in the UV-B region and are known for cosmetic preparations, as sunscreen agents, with the compounds of the formula I usually being employed in a smaller amount than the UV-B-absorbing compounds.

Most of the sunscreen agents in cosmetic preparations used to protect the human epidermis consist of compounds which absorb UV light in the UV-B region, ie. in the range from 280 to 320 nm. For example, the amount of the UV-A absorbers to be used according to the invention is 10–90% by weight, preferably 20–50% by weight, based on the total amount of UV-B- and UV-A-absorbing substances.

All UV-B filter substances are suitable as UV-B filter substances used in combination with the compounds of the formula I to be used according to the invention. Examples which may be mentioned are:

| No. | Substance | CAS No. (=acid) |
|---|---|---|
| 1 | 4-aminobenzoic acid | 150-13-0 |
| 2 | 3-(4-trimethylammoniobenzylidene)-2-bornanone methyl sulfate | 52793-97-2 |
| 3 | 3,3,5-trimethylcyclohexyl salicylate (homosalate) | 118-56-9 |
| 4 | 2-hydroxy-4-methoxybenzophenone (oxybenzone) | 131-57-7 |
| 5 | 2-phenylbenzimidazole-5-sulfonic acid and its potassium, sodium and triethanolamine salts | 27503-81-7 |
| 6 | 3,3'-(1,4-phenylenedimethine)bis(7,7-dimethyl-2-oxobicyclo[2.2.1]heptane-1-methanesulfonic acid) and its salts | 90457-82-2 |
| 7 | Polyethoxyethyl 4-bis(polyethoxy)aminobenzoate | 113010-52-9 |
| 8 | 2-ethylhexyl 4-dimethylaminobenzoate | 21245-02-3 |
| 9 | 2-ethylhexyl salicylate | 118-60-5 |
| 10 | 2-isoamyl 4-methoxycinnamate | 7/6/7-10-2 |
| 11 | 2-ethylhexyl 4-methoxycinnamate | 5466-77-3 |
| 12 | 2-hydroxy-4-methoxybenzophenone-5-sulfonic acid (sulisobenzone) and the sodium salt | 4065-45-6 |
| 13 | 3-(4-sulfobenzylidene)-2-bornanone and salts | 58030-58-6 |
| 14 | 3-(4-methylbenzylidene)-2-bornanone | 36861-47-9 |
| 15 | 3-benzylidene-2-bornanone | 16087-24-8 |
| 16 | 1-(4-isopropylphenyl)-3-phenyl-1,3-propanedione | 63260-25-9 |
| 17 | 4-isopropylbenzyl salicylate | 94134-93-7 |
| 18 | 2,4,6-tri(o-2-ethylhexoxycarbonylanilino)-1,3,5-triazine | 88122-99-0 |
| 19 | 3-(4-imidazol-4-yl)acrylic acid and its ethyl ester | 104-98-3* |
| 20 | ethyl 2-cyano-3,3-diphenylacrylate | 5232-99-5 |
| 21 | 2-ethylhexyl 2-cyano-3, 3-diphenylacrylate | 6197-30-4 |
| 22 | menthyl o-aminobenzoate or: 5-methyl-2-(1-methylethyl)cyclohexyl 2-aminobenzoate | 134-09-8 |
| 23 | glyceryl p-aminobenzoate or: 4-aminobenzoic acid 1-glyceryl ester | 136-44-7 |
| 24 | 2,2'-dihydroxy-4-methoxybenzophenone (dioxybenzone) | 131-53-3 |
| 25 | 2-hydroxy-4-methoxy-4'-methylbenzophenone (mexenone) | 1641-17-4 |
| 26 | triethanolamine salicylate | 2174-16-5 |
| 27 | dimethoxyphenylglyoxalic acid or: sodium 3,4-dimethoxyphenylglyoxalate | |
| 28 | 3-(4-sulfobenzylidene)-2-bornanone and its salts | 56039-58-8 |

Finally, mention should also be made of micronized pigments such as titanium dioxide and zinc oxide.

The compounds to be used according to the invention are usually distinguished by particularly high absorbance in the UV-A region. In addition they are very soluble in cosmetic oils and can easily be incorporated into cosmetic formulations. Emulsions prepared with the compounds I are distinguished in particular by high stability, and the compounds I themselves by their high photostability, and the preparations produced with I by their pleasant skin feel.

EXAMPLES

Example 1 (preparation)

General method:

One mole of the compound of the formula III (cyanomethyl ketone) is dissolved with one mole of the compound of the formula IV (aldehyde or ketone) in methanol, 10 ml each of piperidine and glacial acetic acid are added to the solution, and it is heated to reflux. The reaction is complete after about 4 h. The precipitated product is filtered off with suction and recrystallized from methanol. Yield about 60–70%.

The compounds prepared in this way are indicated in Table 1.

TABLE 1

| No. | Compound | $\lambda_{max.}$ [nm] in EtOH | $E_1^1$ |
|---|---|---|---|
| 1 | (structure) | 348 | 910 |
| 2 | (structure) | 366 | 721 |
| 3 | (structure) | 366 | 967 |
| 4 | (structure) | 338 | 541 |
| 5 | (structure) | 358 | 844 |

TABLE 1-continued

| No. | Compound | $\lambda_{max.}$ [nm] in EtOH | $E_1^1$ |
|---|---|---|---|
| 6 | (structure) | 346 | 1346 |
| 7 | (structure) | 348 | 1039 |
| 8 | (structure) | 352 | 936 |

General method for preparing emulsions for cosmetic purposes

All the oil-soluble ingredients are heated to 85° C. in a stirred vessel. When all the ingredients have melted and are in the form of a liquid phase, the aqueous phase is incorporated by homogenization. The emulsion is cooled to about 40° C. while stirring, perfume is added and, after homogenization, the mixture is cooled to 25° C. while stirring continuously.

Preparations

Example 2

| Composition for lip care | |
|---|---|
| ad 100 | Eucerinum anhydricum |
| 10.00 | Glycerol |
| 10.00 | Titanium dioxide |
| 0.5–10 | Compound No. 1 in Table 1 |
| 8.00 | Octyl methoxycinnamate |
| 5.00 | Zinc oxide |
| 4.00 | Castor oil |
| 4.00 | Pentaerythritol stearate/caprate/caprylate/adipate |
| 3.00 | Glyceryl stearate SE |
| 2.00 | Beeswax |
| 2.00 | Microcrystalline wax |
| 2.00 | Quaternium-18 bentonite |
| 1.50 | PEG-45/dodecyl glycol copolymer |

Example 3

| Composition for sunblocker with micropigments | |
|---|---|
| ad 100 | Water |
| 10.00 | Octyl methoxycinnamate |
| 6.00 | PEG-7 hydrogenated castor oil |
| 6.00 | Titanium dioxide |
| 0.5–10 | Compound No. 2 in Table 1 |
| 5.00 | Mineral oil |
| 5.00 | Isoamyl p-methoxycinnamate |
| 5.00 | Propylene glycol |
| 3.00 | Jojoba oil |
| 3.00 | 4-Methylbenzylidenecamphor |
| 2.00 | PEG-45/dodecyl glycol copolymer |
| 1.00 | Butylmethoxydibenzoylmethane |
| 1.00 | Dimethicone |
| 0.50 | PEG-40 hydrogenated castor oil |
| 0.50 | Tocopheryl acetate |
| 0.50 | Phenoxyethanol |
| 0.20 | EDTA |

Example 4

| Fat-free gel | |
|---|---|
| ad 100 | Water |
| 8.00 | Octyl methoxycinnamate |
| 7.00 | Titanium dioxide |
| 0.5–10 | Compound No. 3 in Table 1 |
| 5.00 | Glycerol |
| 5.00 | PEG-25 PABA |
| 1.00 | 4-Methylbenzylidenecamphor |
| 0.40 | Acrylate C10–C30 alkylacrylate crosspolymer |
| 0.30 | Imidazolidinylurea |
| 0.25 | Hydroxyethylcellulose |
| 0.25 | Sodium methylparaben |
| 0.20 | Disodium EDTA |
| 0.15 | Fragrance |
| 0.15 | Sodium propylparaben |
| 0.10 | Sodium hydroxide |

Example 5

| Suncream (SPF 20) | |
|---|---|
| ad 100 | Water |
| 8.00 | Octyl methoxycinnamate |
| 8.00 | Titanium dioxide |
| 6.00 | PEG-7 hydrogenated castor oil |
| 0.5–10 | Compound No. 1 in Table 1 |
| 6.00 | Mineral oil |
| 5.00 | Zinc oxide |
| 5.00 | Isopropyl palmitate |
| 5.00 | Imidazolidinylurea |
| 3.00 | Jojoba oil |
| 2.00 | PEG-45/dodecyl glycol copolymer |
| 1.00 | 4-Methylbenzylidenecamphor |
| 0.60 | Magnesium stearate |
| 0.50 | Tocopheryl acetate |
| 0.25 | Methylparaben |
| 0.20 | Disodium EDTA |
| 0.15 | Propylparaben |

Example 6

| Water-fast sun cream | |
|---|---|
| ad 100 | Water |
| 8.00 | Octyl methoxycinnamate |
| 5.00 | PEG-7 hydrogenated castor oil |
| 5.00 | Propylene glycol |
| 4.00 | Isopropyl palmitate |
| 4.00 | Caprylic/capric triglyceride |
| 0.5–10 | Compound No. 1 in Table 1 |
| 4.00 | Glycerol |
| 3.00 | Jojoba oil |
| 2.00 | 4-Methylbenzylidenecamphor |
| 2.00 | Titanium dioxide |
| 1.50 | PEG-45/dodecyl glycol copolymer |
| 1.50 | Dimethicone |
| 0.70 | Magnesium sulfate |
| 0.50 | Magnesium stearate |
| 0.15 | Fragrance |

Example 7

| Sun milk (SPF 6) | |
|---|---|
| ad 100 | Water |
| 10.00 | Mineral oil |
| 6.00 | PEG-7 hydrogenated castor oil |
| 5.00 | Isopropyl palmitate |
| 3.50 | Octyl methoxycinnamate |
| 0.5–10 | Compound No. 2 in Table 1 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |
| 0.15 | Propylparaben |
| 0.05 | Tocopherol |

We claim:

1. A compound represented by formula II:

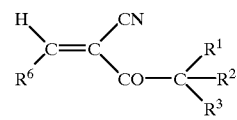

II wherein $R^1$, $R^2$ and $R^3$ are low molecular weight alkyl radicals, and $R^6$ is a $R^6$ is a 2-thienyl radical optionally substituted with low molecular weight alkyl radicals or is is a (3,5-di-t-butyl)-4-alkoxyphenyl radical.

2. The compound of claim 1, wherein $R^6$ is a 2-thienyl radical optionally substituted with low molecular weight alkyl radicals.

3. The compound of claim 1, wherein $R^6$ is a (3,5-di-t-butyl)-4-hydroxyl phenyl radical.

4. The compound of claim 1, wherein $R^6$ is an unsubstituted 2-thienyl radical.

5. The compound of claim 1, wherein $R^6$ is a 2-thienyl radical substituted with low molecular weight alkyl radicals.

6. The compound of claim 1, wherein $R^1$, $R^2$ and $R^3$ have 1 to 4 carbon atoms.

7. The compound of claim 1, wherein $R^1$, $R^2$ and $R^3$ are each methyl.

8. The compound of claim 2, wherein $R^1$, $R^2$ and $R^3$ are each methyl.

9. The compound of claim 3, wherein $R^1$, $R^2$ and $R^3$ are each methyl.

10. The compound of claim 1, wherein $R^6$ is a 2-thienyl radical substituted with a methyl radical.

11. A cosmetic composition, comprising the compound of claim 1 and a cosmetically acceptable carrier.

12. The cosmetic composition of claim 11, wherein the cosmetically acceptable carrier comprises an oil phase.

13. The cosmetic composition of claim 11, which is a sunscreen.

14. A method of protecting skin from UV radiation, comprising applying an effective amount of the compound of claim 1 to the skin.

15. A method of protecting skin from UV radiation, comprising applying an effective amount of the composition of claim 11 to the skin.

* * * * *